US00RE34519E

United States Patent [19]

Fox et al.

[11] E Patent Number: Re. 34,519

[45] Reissued Date of Patent: Jan. 25, 1994

[54] SURGICAL STAPLER CARTRIDGE LOCKOUT DEVICE

[75] Inventors: William D. Fox, New Richmond; Rudolph H. Nobis, Cincinnati; Richard P. Nuchols, Beavercreek; Mark S. Zeiner, Cincinnati, all of Ohio

[73] Assignee: Ethicon, Inc., Cincinnati, Ohio

[21] Appl. No.: 815,235

[22] Filed: Dec. 31, 1991

Related U.S. Patent Documents

Reissue of:

[64] Patent No.: 4,892,244
Issued: Jan. 9, 1990
Appl. No.: 267,907
Filed: Nov. 7, 1988

[51] Int. Cl.[5] ..... A61B 17/072

[52] U.S. Cl. ..... 227/176; 227/8; 227/19; 227/178; 227/180

[58] Field of Search ..... 227/19, 175, 176, 177, 227/178, 179, 180, 181, 182, 8

[56] References Cited

U.S. PATENT DOCUMENTS

| | | | |
|---|---|---|---|
| 2,174,219 | 9/1939 | Balma | 1/49 |
| 2,246,647 | 6/1941 | Vancura | 1/49 |
| 3,079,606 | 3/1963 | Bobrov et al. | 1/120 |
| 3,490,675 | 1/1970 | Green et al. | 227/19 |
| 3,499,591 | 3/1970 | Green | 227/76 |
| 3,844,289 | 10/1974 | Noiles | 128/334 R |
| 4,086,926 | 5/1978 | Green et al. | 128/344 R |
| 4,202,480 | 5/1980 | Annett | 227/8 |
| 4,256,251 | 3/1981 | Moshofsky | 227/120 |
| 4,304,236 | 12/1981 | Conta et al. | 227/19 X |
| 4,391,401 | 7/1983 | Moshofsky | 227/19 |
| 4,473,077 | 9/1984 | Noiles | 128/305 |
| 4,519,532 | 5/1985 | Foslien | 227/8 |
| 4,520,817 | 6/1985 | Green | 227/76 X |
| 4,569,346 | 2/1986 | Poirier | 128/305 |
| 4,576,167 | 3/1986 | Noiles | 128/334 |
| 4,591,085 | 5/1986 | Giovanni | 227/8 |
| 4,633,861 | 1/1987 | Chow et al. | 227/19 |
| 4,646,745 | 3/1987 | Noiles | 128/344 R |
| 4,664,305 | 5/1987 | Blake, III et al. | 227/121 X |
| 4,809,898 | 3/1989 | Gassner et al. | 227/8 |

OTHER PUBLICATIONS

Auto Suture Disposable EEA Surgical Stapler, United States Surgical Corporation, 1984 (Information Booklet).

*Primary Examiner*—Rinaldi I. Rada
*Attorney, Agent, or Firm*—Dressler, Goldsmith, Shore & Milnamow, Ltd.

[57] ABSTRACT

A lockout mechanism actuable upon the firing of staples in a surgical staple cartridge such that the lockout mechanism prevents the refiring of the spent staple cartridge when the cartridge remains loaded within the surgical stapler. In addition, the lockout mechanism will prevent reloading of a spent staple cartridge within a surgical stapler after the spent staple cartridge has been removed from the surgical stapler.

23 Claims, 6 Drawing Sheets

SURGICAL STAPLER CARTRIDGE LOCKOUT DEVICE

Matter enclosed in heavy brackets [ ] appears in the original patent but forms no part of this reissue specification; matter printed in italics indicates the additions made by reissue.

FIELD OF THE INVENTION

This invention is generally related to a device for prevention of refiring or surgical staplers. More specifically, this invention is related to a device which prevents the refiring and reloading of a spent staple cartridge in a surgical stapler.

BACKGROUND OF THE INVENTION

Surgical staplers have become a very typical form of wound closure during surgery. These surgical staplers can perform various functions such as closing internal wounds, as well as suturing skin. Many of these surgical staplers have reloadable cartridges. These cartridges allow for the rapid reloading of the surgical stapler during the operation. That is, the stapler can be used, the spent cartridge removed, and the surgical stapler reloaded with another cartridge and ready for use.

One problem, however, is the refiring of staplers containing spent cartridges. In other words, during the course of surgery it may be possible for the surgeon to use the surgical stapler and then inadvertently not reload the stapler with an unused cartridge. The stapler is then inserted into the wound for use, and then fired. Of course, because the cartridge is already spent, the stapler will not be able to fire another round of staplers. This results in a delay while reloading the surgical stapler.

SUMMARY OF THE INVENTION

It is therefore an object of the present invention to Provide a means with which to prevent a spent staple cartridge from being fired.

It is further an object of the present invention to provide a means with which to prevent a spent staple cartridge from being unloaded from a surgical stapler and then being reloaded into any other surgical stapler.

It is yet another object of the present invention to provide an indicating means to show that a staple cartridge has been fired.

It is further an object of the present invention to provide a means within which a user will know whether a staple cartridge has not been fired.

Finally, it is an object of the present invention to provide a means by which a lock-out mechanism prevents the firing apparatus in a stapler from being used within a staple cartridge after the cartridge has been spent.

These and other objects of the invention are accomplished in a lock-out mechanism in a surgical stapler cartridge. The lock-out mechanism comprises a device actuable upon the firing of the staples by the stapler. The lock-out mechanism also prevents the refiring of the stapler when loaded with the spent cartridge.

The lock-out mechanism is generally a spring loaded device which is actuated during firing other staples to cause a barrier to be placed within the path of the firing mechanism. In addition, the device of the present invention includes a reloading barrier actuable upon the same firing. This reloading barrier will prevent an unloaded staple cartridge from being reloaded into a surgical stapler. This is accomplished by a mechanism which causes the staple cartridge to become too wide to allow emplacement within the surgical stapler.

BRIEF DESCRIPTION OF THE DRAWINGS

The objects of of the present invention will be more fully described in the following detailed description of the invention when taken in conjunction with the accompanying drawings wherein.

DETAILED DESCRIPTION OF THE DRAWINGS

Figure 1:
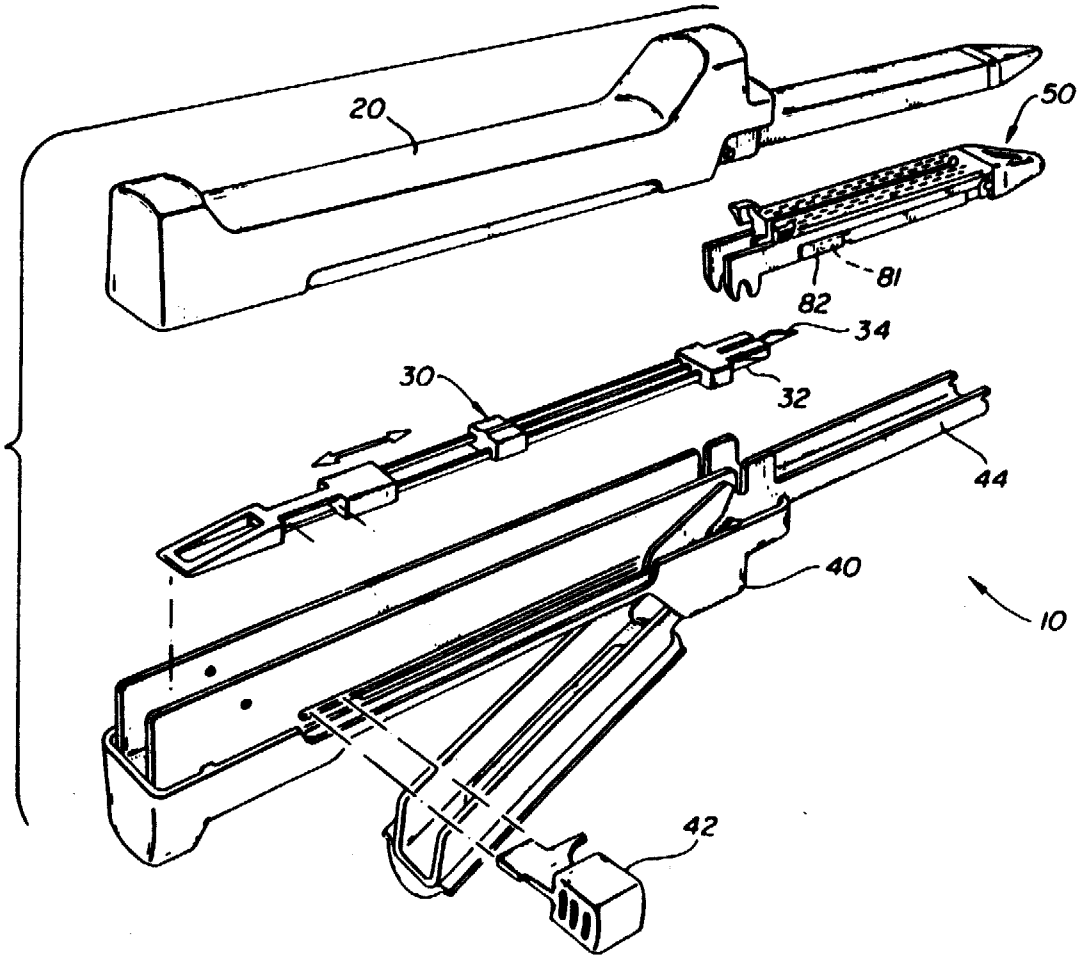
FIG. 1 is an exploded view in perspective of a surgical stapler loaded with a cartridge containing the lockout mechanism of the present invention.
Figure 2:
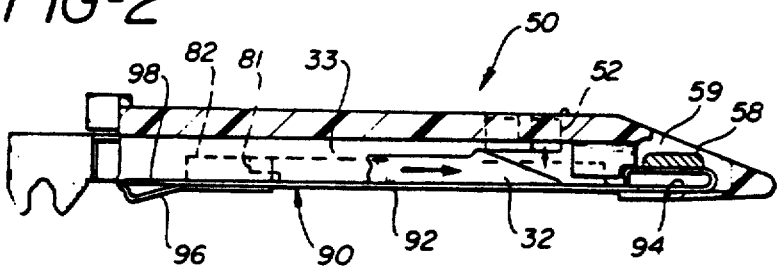
FIG. 2 is an elevation view of the lockout mechanism of the present invention during actuation of the lockout mechanism at the beginning of the stroke of the surgical stapler.
Figure 3:
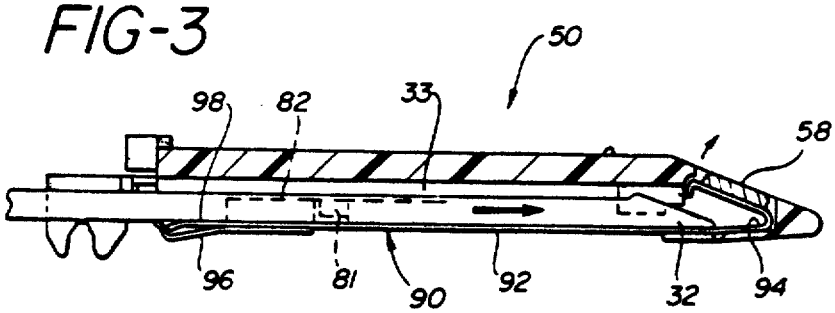
FIG. 3 is an elevation view and partial cross section of the invention further along the stroke.
Figure 4:
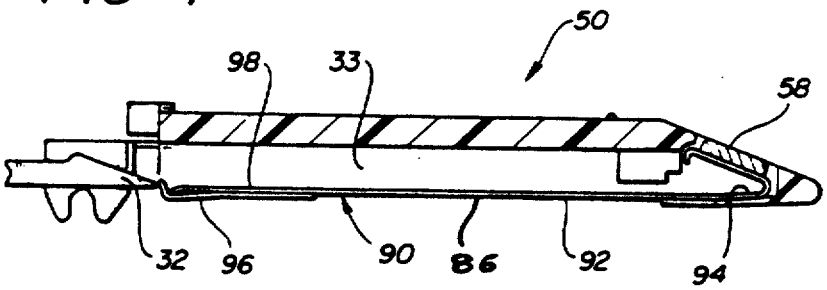
FIG. 4 is an elevation view and partial cross section with the firing mechanism activated and the surgical stapler unable reloaded.
Figure 5:
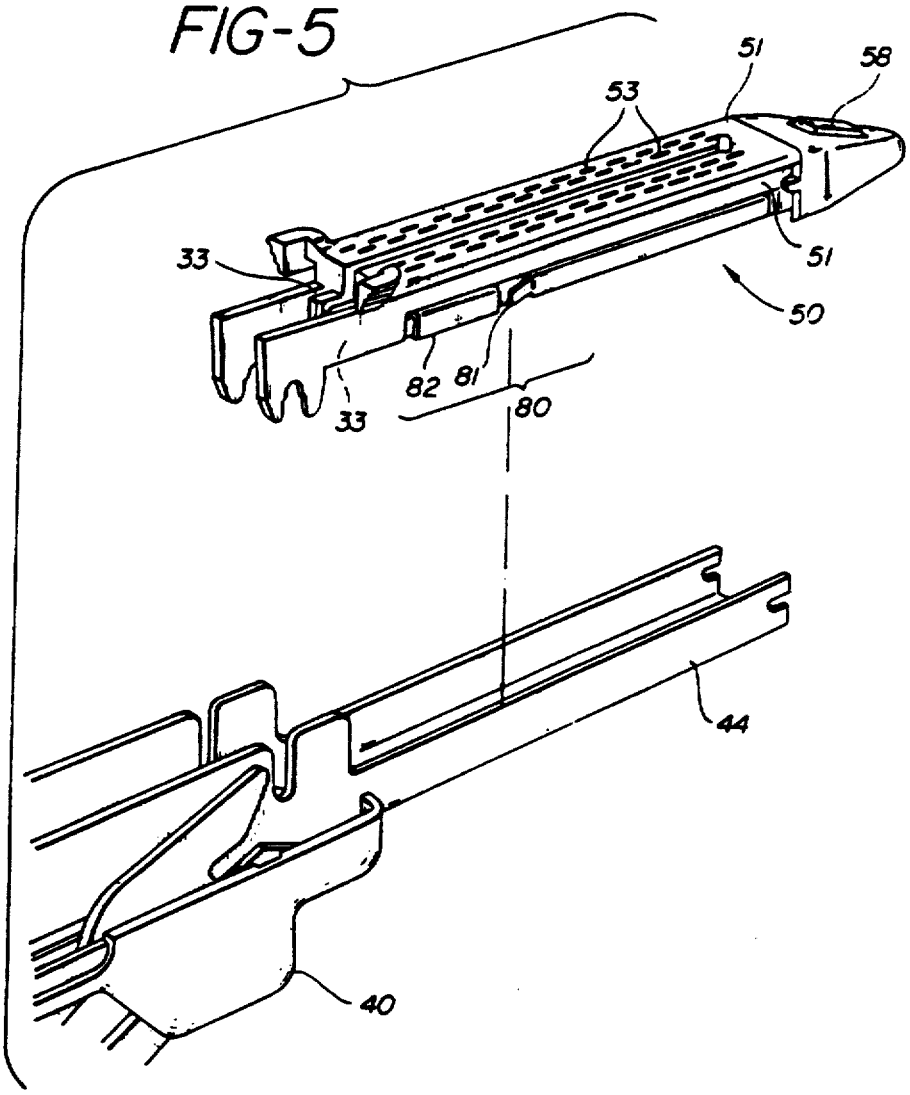
FIG. 5 is an exploded view in perspective of the surgical staple cartridge with the lockout mechanism activated.

As seen in FIG. 1, a typical surgical stapler 10 will have an upper jaw 20, firing means 30, a lower jaw of 40 and a staple cartridge 50 which fits within the lower jaw 40. *The upper jaw 12 and lower jaw 40 form a typical frame means of the stapler 10.* The firing means 30 will generally comprise a pusher bar or firing wedge 32, as best seen in FIGS. 2, 3, and 4. Returning to FIG. 1, the firing means 30 will also contain a knife 34 which generally will be placed between the firing wedges 32. The firing wedges 32 will fit within longitudinal slots 33 located on the staple cartridge 50, as best seen in FIG. 5. Continuing with FIG. 5, the cartridge 50 will contain parallel side walls 51 which fit within the lower jaw channel 44. As seen in FIG. 1, a firing knob 42 activates the firing means 30 in order to send the firing wedges 32 through the staple cartridge 50.

Figure 6:
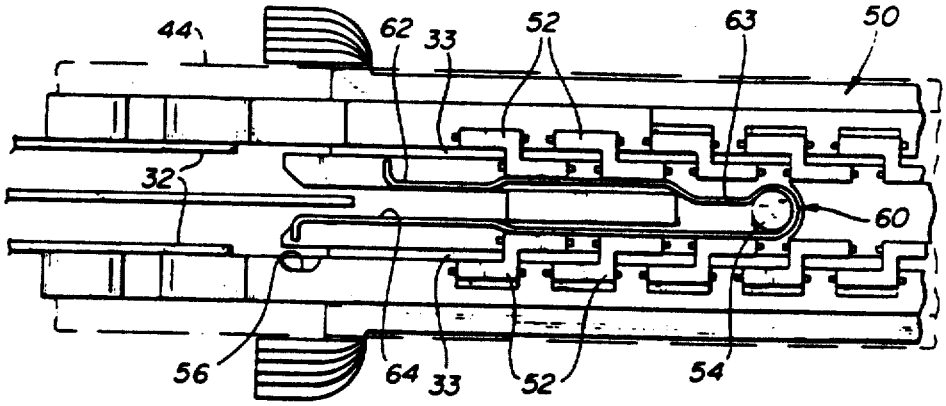
FIG. 6 is a top plan view of a preferred embodiment of a preloaded lockout mechanism of the present invention.
Figure 8:
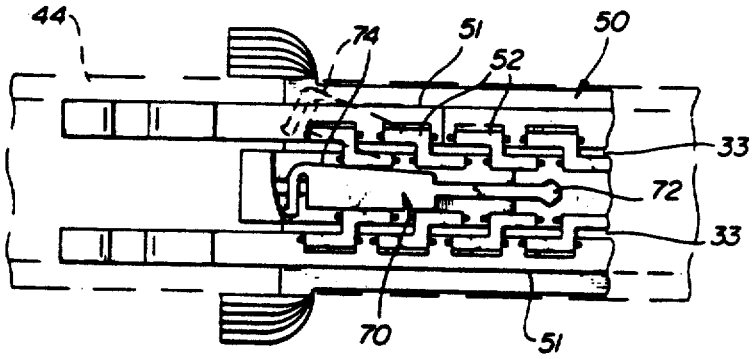
FIG. 8 is a top plan view of a preferred embodiment of the present invention shown in both the loaded and lockout positions.

When the firing wedges 32 pass through the longitudinal slots 33 in the staple cartridge 50, the firing wedges 32 come into contact with drivers 52. These drivers 52 are best seen in FIG. 6 or FIG. 8. The drivers 52 will activate staples not shown so that the staples will be ejected from the slots 53 seen in FIG. 5. On the upper jaw 20, there is an anvil not shown which will form the staples when they are driven through the slots 53.

One aspect of the present invention is seen in FIGS. 2, 3 and 4. When the firing wedge 32 travels through the staple cartridge 50, and is activating drivers 52, it will come into contact with a lockout mechanism 90. This lockout mechanism 90 is comprised of a strip 92 which has a front end 94. This front end 94 is spring loaded and sits within a hollow 59 of the staple cartridge 50. When the firing wedge 32 advances far enough into the staple cartridge 50, the front end 94 of the strip 92 is activated so that it moves entirely within the hollow 59. An indicator flag 58 is then activated to demonstrate the firing of the staples. When this strip 90 continues to move forward in the staple cartridge 50, a detent *or restraining* means 98 is moved away from a barrier lock 96, as seen in FIG. 3. When the firing wedges 32 are retracted from the staple cartridge 50, the barrier lock 96 is able to move into the path of the firing wedge 32, as seen in FIG. 4. At this point, therefore, the firing wedge 32 is no longer able to move through the longitudinal slots 33 of the staple cartridge, because it is blocked by the barrier lock 96. Thus, the lockout mechanism 90 prevents refiring of the spent staple cartridge 50. Of course, because the indicator flag 58 is activated, the user acknowledges this fact and can reload the stapler 10 with a new unused staple cartridge 50.

An additional aspect of the lockout mechanism of the present invention is shown in FIG. 5. There is seen lockout spring or barrier 80. This barrier 80 comprises ears 81 which are fit under a cover or sleeve 82. The ears 81 are urged away from the staple cartridge 50 by means of a spring 84, which is generally a leaf spring integral with the lockout mechanism 80. When the strip 92 is moved forward in the staple cartridge 50 to activate the indicator flag 58 (also shown in FIG. 5), the outer wall 86 of the strip 92 also moves forward. This causes the ears 81 to be displaced from beneath the cover or sleeve 82. Of course, because the staple cartridge is seated within the lower jaw channel 44, the ears 81 are not displaced away from the sides of the walls 51 of the staple cartridge 50. However, when the staple cartridge 50 is removed from the stapler 10, the ears 81 are activated by the leaf spring 84 in order to be displaced away from the walls 51. At this point, then, the staple cartridge 50 is no longer insertable within the lower jaw channel 44. Again, the indicator flag 58 has been activated to show that the staple cartridge 50 is spent. Thus, the user is prevented from reloading the spent staple cartridge 50 and will only be able to load an unused staple cartridge 50.

Figure 7:
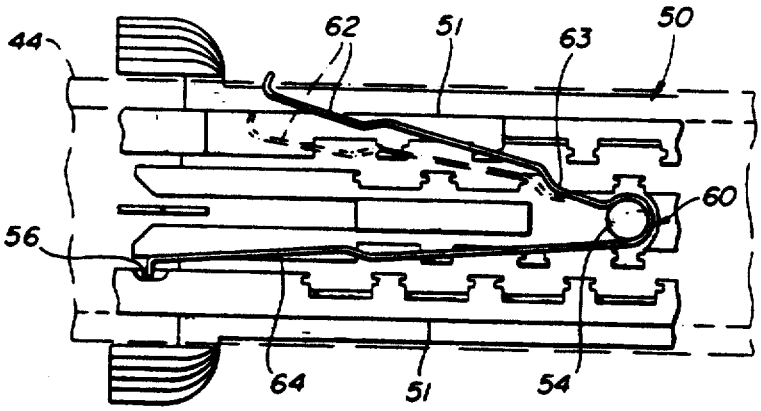
FIG. 7 is a top plan view of a preferred embodiment of the lockout mechanism of the present invention in lockout position.

Another aspect of the lockout mechanism of the present invention is demonstrated in FIGS. 6 and 7. Here is seen firing barrier 60. This firing barrier 60 comprises a spring loaded blocking leg 62 and a base leg 64. This spring loaded blocking leg 62 is generally urged away from the base leg 64 by a first spring 63, which will generally be a leaf spring similar to the leaf spring 84 in the lockout mechanism 80.

When the staple cartridge has yet to be fired, the drivers 52 in the staple cartridge hold the firing barrier 60 between the drivers 52. The firing barrier 60 is held in place around a knob 54 molded into the staple cartridge 50. When the firing wedges 32 pass through the staple cartridge 50 in order to activate the drivers 52, the drivers 52 are moved down these slots 53 so that the area once occupied by the drivers 52 is evacuated. When this happens, the spring loaded blocking leg 62 is able to be moved by the first spring 63 away from the base leg 64. In addition, the base leg 64 is also able to be moved within a cut-out 56 made in the staple cartridge 50.

This position of the firing barrier 60 will prevent the refiring of the pusher bars or firing wedges 32 after they have been retracted from the staple cartridge 50. In addition, because the spring loaded blocking legs 62 will generally have a resting position wider than the width of the staple cartridge 50, when the staple cartridge 50 is removed from the lower jaw channel 44 of the surgical stapler 10, the spring loaded blocking leg 62 will rest in a wider position than the staple cartridge 50. This prevents reloading of the spent staple cartridge 50, so that only an unused staple cartridge 50 can be inserted into the surgical stapler 10.

Figure 9:
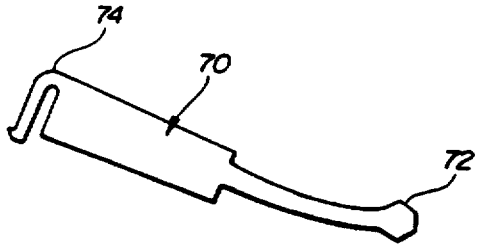
FIG. 9 is a top plan view of the preferred embodiment of the present invention.

A further aspect of the present invention can be seen in FIGS. 8 and 9. This aspect comprises firing barrier 70 which operates much on the same basis as firing barrier 60. The firing barrier 760 contains a spring-loaded base 72 which is held in place within the staple cartridge 50. There is also a blocking portion 74 which is generally urged by the spring-loaded base 72 to a position in the path of the firing wedges 32. Generally, the drivers 52 will hold the firing barrier 70 in place between the drivers 52. However, when the firing wedge 32 activates the drivers 52, the firing barrier 70 is urged into the path of the firing wedges 32. At that point, the firing wedges 32 can no longer pass through the staple cartridge 50. The spent staple cartridge 50 must be replaced with a unused staple cartridge 50.

Figure 10:
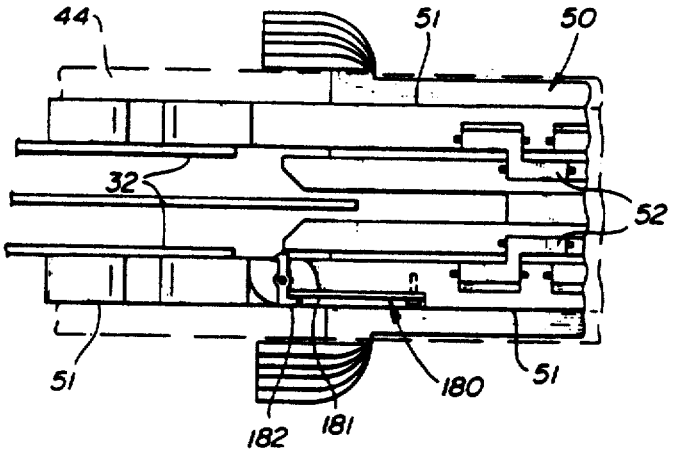
FIG. 10 is an additional preferred embodiment of the lockout barrier aspect of the present invention.
Figure 11:
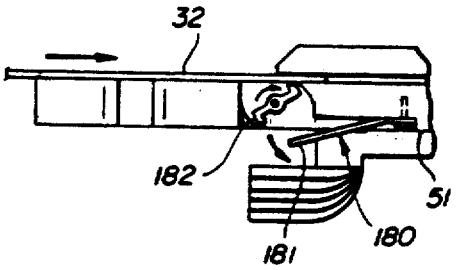
FIG. 11 is a partial view of the actuated barrier aspects of the present invention.

One final aspect of the present invention is shown in FIGS. 10 and 11. There is shown a reloading barrier 180, comprised ears 181 and pivoting cover 182. The ears 181 are generally urged by a spring force outside the walls 51 of the staple cartridge 50. Generally, the pivoting cover 182 holds the ear 181 in place within the walls 51 of the staple cartridge 50. However, when the firing wedge 32 of the firing means 30 is sent through the staple cartridge 50 to activate the drivers 52, the firing wedge 32 also comes into contact with the pivoting cover 182. This causes the ears 181 of the staple cartridge to be urged by their spring force to a position where they will remain outside of the walls 51 of the staple cartridge 50. Thus, when the staple cartridge 50 is removed from the lower jaw channel 44 of the surgical stapler 10, the ears 181 relax to a point where they become wider than the width of the staple cartridge 50. This prevents reloading of the staple cartridge 50 within the lower jaw channel 44 of the surgical stapler 10. Only an unused staple cartridge 50 will be able to be loaded into the stapler 10.

The unique combination of features possessed by the present invention render them well suited for use within a surgical stapler, in order to prevent refiring or reloading of a spent surgical staple cartridge. This enhances speed and time of performance for the surgeon. Naturally, these combinations may be useful for other types of cartridge-loading mechanisms. Of course, while several means are available, the particular advantageous embodiments have been chosen to illustrate the invention. It will be understood by those skilled in the art that various changes and modifications may be made in the invention without departing from its scope, which is defined by the following claims and their equivalents.

What is claimed is:

[1. In a surgical stapler having firing means for firing staples and in which a removable cartridge containing staples may be loaded and replaced by another removable cartridge, a lockout mechanism on said stapler actuable by said firing means upon the firing of said staples by said stapler such that said lockout mechanism blocks said firing means and prevents the refiring of said stapler when loaded with said spent cartridge.]

[2. The stapler of claim 1, said lockout mechanism further being spring loaded before the firing of said staples, such that upon said firing, said spring is actuated by contact between said firing means and said lockout mechanism to cause said lockout mechanism to enter said firing means path after retraction of said firing means to prevent the refiring of said firing means into said spent cartridge.]

[3. In a cartridge containing surgical staples and a path wherein a firing means from a surgical stapler can move in order to fire said stapler, a lockout mechanism comprising a firing barrier loaded by a first spring, said barrier preloaded on said cartridge before the insertion of said cartridge into a surgical stapler, said first spring actuable upon the firing of said stapler by said firing means located on said stapler, such that said barrier is caused by said first spring to move into said path to prevent the refiring of said staples loaded with said spent cartridge.]

4. [The lockout mechanism of claim 3 further comprising] *In a cartridge containing surgical staples and a path wherein a firing means from a surgical stapler can move in order to fire said stapler, a lockout mechanism comprising a firing barrier loaded by a first spring, said barrier preloaded on said cartridge before the insertion of said cartridge into a surgical stapler, said first spring actuable upon the firing of said stapler by said firing means located on said stapler, such that said barrier is caused by said first spring to move into said path to prevent the refiring of said staples loaded with said spent cartridge, and* a reloading barrier movable between a firing position in which said reloading barrier is loaded by a second spring, and a blocking position, such that the firing of said firing means activates said second spring to cause said reloading barrier to pass from said firing position to said blocking position, said reloading barrier in said blocking position capable of preventing the reloading of said spent cartridge in any stapler upon the removable of said spent cartridge from said stapler.

5. The lockout mechanism of claim 4 further comprising an indicator flag actuable upon the firing of said staples to indicate said firing.

6. In a staple cartridge insertable within a surgical stapler and containing staples and comprising an elongated body including one or more longitudinal slots for slidably receiving one or more longitudinal pusher bars comprising a firing mechanism of said surgical stapler, and a plurality of drivers engageable by said pusher bars for ejecting the staples from the cartridge, said staple cartridge releasably fastened to a said surgical stapler, the improvement comprising a lockout mechanism connected to said longitudinal slots for preventing said pusher bars from passing more than one time through said longitudinal slots.

7. In the staple cartridge of claim 6, the lockout mechanism comprising a strip slidable within said cartridge comprising:

a front end emplaced within a narrow hollow located toward the front of said cartridge, said front end comprising a folded spring loaded strip such that said pusher bars can contact said front end and cause said front end to slide further toward the front of said cartridge such that said spring is actuated to open within said hollow; and a spring loaded barrier lock located on the rear end of said strip, said barrier lock placed under a detent means within said cartridge in order to avoid contact with said pusher bars, said barrier lock loosened from said detent means upon the sliding of said front end, such that said barrier lock moves within the path of said pusher bars to prevent said pusher bars from passing within said cartridge upon the retraction of said pusher bars from said cartridge.

8. In the staple cartridge of claim 7, said cartridge held within a narrow channel of said stapler, said cartridge having parallel side walls fitting within said narrow channel, the improvement further comprising a lockout spring attached to the side walls of said cartridge, said lockout spring comprising a resilient ear held in place by a cover moved by said pusher bars upon the actuation of said stapler to expose said ear, such that said ear becomes urged outside the width of said channel upon the removal of said cartridge, to prevent reinsertion of said spent cartridge within said channel.

9. The staple cartridge of claim 8 wherein said cover is pivotable within said cartridge such that the pivoting of said cover causes the exposing of said ears.

10. In the staple cartridge of claim 8, the improvement further comprising an indicator flag actuable by said folded spring loaded strip to emerge from said hollow upon the firing of staples.

11. In the staple cartridge of claim 6, the improvement comprising a spring loaded bar emplaced within and held by said drivers such that when said pusher bar engages said drivers to activate said staples and said pusher bar is retracted from said cartridge, said spring loaded bar moves into the path of said pusher bars to prevent motion of said pusher bars with said cartridge.

12. In the cartridge of claim 11, the lockout mechanism further comprising said spring loaded bar having a resting position beyond the width of said cartridge upon the firing of said staples, the activation of said bar and the removal of said cartridge from said stapler, such that said bar prevents the reinsertion of said cartridge into said stapler.

*13. A surgical stapler comprising: a cartridge having a plurality of staples frame means, for carrying said cartridge, firing means including a pusher assembly movable relative to said frame means in an initial longitudinal firing movement of the pusher assembly down a path to fire the staples, a lockout mechanism for preventing a subsequent longitudinal firing movement of the pusher assembly after the pusher assembly has been moved to a retracted position by longitudinal movement of said pusher assembly along said path in a direction opposite to a direction of said firing movement, said lockout mechanism including barrier means for preventing refiring movement of said pusher assembly, said barrier means being movable from a first position to a second position, and restraining means for blocking said barrier means to maintain said barrier means in said first position thereof so that said pusher assembly can be advanced along said path to effect firing of said staples, said restraining means being movable in response to firing movement of said pusher assembly relative to said frame means so that said barrier means is movable to said second position to prevent refiring after the pusher assembly has been moved to said retracted position.*

*14. A surgical stapler as set forth in claim 13 in which said frame means comprises an upper and lower jaw member.*

*15. A surgical stapler comprising: a cartridge having a plurality of staples, and a plurality of movable drivers for firing said staples, frame means for carrying said cartridge, said cartridge defining at least one longitudinal slot, firing means including a pusher assembly movable relative to said frame means, said pusher assembly including at least one pusher bar movable within said longitudinal slot for engaging said movable drivers, and for moving said drivers in a direction perpendicular to the direction of movement of said pusher bar, a lockout mechanism for preventing firing movement of the pusher assembly after the pusher assembly has been moved to a retracted position by longitudinal movement of said pusher assembly along said path in a direction opposite to a direction of said firing movement, said lockout mechanism including barrier means for preventing refiring movement of said pusher assembly, said barrier means being movable from a first position to a second position for preventing movement of the pusher assembly from said retracted position when the barrier means is in said second position, and restraining means separate from and responsive to movement of said pusher bar along said path for blocking said barrier means to maintain said barrier means in said first position thereof so that said pusher assembly can be advanced along said path to effect firing of said staples by engagement of said pusher bar with said drivers, said restraining means being movable in response to firing movement of said pusher assembly relative to said frame means so that said barrier means is movable to said second position to prevent refiring after the pusher assembly has been moved to said retracted position.*

*16. A surgical stapler in accordance with claim 15, where the barrier means includes resilient projecting means biased from said first position toward said second position wherein in said second position said projecting means projects into the path of said pusher assembly and prevents movement of said pusher assembly from the retracted position thereof relative to said frame means by engagement of said resilient projecting means with said pusher assembly.*

*17. A surgical stapler comprising a staple-filled cartridge having one or more slots, frame means for carrying said cartridge, a firing means including a pusher assembly movable relative to said frame means, said pusher assembly comprising one or more pusher bars respectively extending through said slots to fire said staples, a firing knob operatively connected to said pusher assembly for moving the pusher assembly in a firing direction down a path to fire the staples, and in a direction opposite said firing direction to a retracted position after at least a portion of the staples have been fired, a lockout mechanism for preventing firing movement of the pusher assembly after the pusher assembly has been moved to the retracted position, said lockout mechanism including barrier means for preventing movement of the pusher assembly from said retracted position, said barrier means comprising resilient projecting means normally biased toward a position to engage said pusher assembly to prevent movement of said pusher assembly relative to said resilient projecting means after said pusher assembly has been moved to said retracted position, and restraining means separate from said pusher bar for blocking said resilient projecting means of said barrier means to maintain said resilient projecting means out of the path of the pusher assembly during staple firing, said restraining means being movable by said pusher assembly during firing movement of the pusher assembly whereby the resilient projecting means of the barrier means is released to allow the resilient projecting means to move into the path of the pusher assembly to prevent firing movement of said pusher assembly after movement thereof to said retracted position.*

*18. A surgical stapler as set forth in claim 17 in which the pusher assembly moves said restraining means to release said barrier means during partial movement of said pusher assembly.*

*19. A surgical stapler as set forth in claim 18 in which the cartridge includes a plurality of movable driers for firing said staples and the drivers comprise the restraining means that preclude the barrier means from moving into position to prevent firing movement of the pusher assembly after it has been moved to a retracted position.*

*20. A surgical stapler as set forth in claim 17 in which the lockout mechanism prevents said pusher bars from passing more than one time through said longitudinal slots.*

*21. A surgical stapler comprising a staple-filled cartridge having one or more slots, frame means for carrying said cartridge, a firing means including a pusher assembly movable relative to said frame means, said pusher assembly comprising one or more pusher bars respectively extending through said slots to fire said staples, a firing knob operatively connected to said pusher assembly for providing an initial longitudinal firing movement of the pusher assembly down a path to fire the staples, and in a direction opposite to a direction of said firing movement to a retracted position after at least a portion of the staples have been fired, a lockout mechanism for preventing a subsequent longitudinal firing movement of the pusher assembly after the pusher assembly has been moved to the retracted position, said lockout mechanism including barrier means for preventing movement of the pusher assembly from said retracted position, said barrier means comprising resilient projecting means normally biased toward a position to engage said pusher assembly to prevent movement of said pusher assembly relative to said resilient projecting means after said pusher assembly has been moved to said retracted position, and restraining means for blocking said resilient projecting means of said barrier means to maintain said resilient projecting means out of the path of the pusher assembly during staple firing, said restraining means being movable by said pusher assembly during said initial longitudinal firing movement of the pusher assembly whereby the resilient projecting means of the barrier means is released to allow the resilient projecting means to move into the path of the pusher assembly to prevent firing movement of said pusher assembly after movement thereof to said retracted position.*

*22. A surgical stapler as set forth in claim 21 in which the pusher assembly moves said restraining means to release said barrier means upon partial movement of the pusher bars through said slots.*

*23. A surgical stapler as set forth in claim 21 in which the pusher assembly moves said restraining means to release said barrier means upon full movement of the pusher bars through said slots.*

*24. A surgical stapler comprising a frame, a cartridge filled with staples and positionable in operative association with said frame and having one or more slots, a firing assemblage including a pusher assembly movable relative to said frame, said pusher assembly comprising one or more pusher bars respectively extending through said slots to fire said staples, a member operatively connected to said pusher assembly for moving the pusher assembly in a firing direction down a path to fire the staples, and in a direction opposite to said firing direction to a retracted position after at least a portion of the staples have been fired, a lockout mechanism for preventing firing movement of the pusher assembly in the firing direction after the pusher assembly has been moved to the retracted position, said lockout mechanism including a barrier assemblage for preventing*

*movement of the pusher assembly from said retracted position, said barrier assemblage comprising a resilient projecting member normally biased toward a position to engage said pusher assembly to prevent movement of said pusher assembly relative to said resilient projecting member after said pusher assembly has been moved to said retracted position, and a restraining structure separate from said pusher bar for blocking said barrier assemblage to maintain said resilient projecting member out of the path of the pusher assembly during staple firing, said restraining structure being movable by said pusher assembly during movement of the pusher assembly in the firing position whereby the barrier assemblage is released to allow the resilient projecting member to move into the path of the pusher assembly to prevent firing movement of said pusher assembly after movement thereof to said retracted position.*

*25. A surgical stapler as set forth in claim 24 in which the pusher assembly moves said restraining structure to release said barrier assemblage upon partial movement of the pusher bars through said slots.*

*26. A surgical stapler as set forth in claim 24 in which the pusher assembly moves said restraining structure to release said barrier assemblage upon full movement of the pusher bars through said slots.*

* * * * *

UNITED STATES PATENT AND TRADEMARK OFFICE

CERTIFICATE OF CORRECTION

PATENT NO. : Re. 34, 519

DATED : January 25, 1994

INVENTOR(S) : William D. Fox, Rudolph H. Nobis, Richard P. Nuchols, and Mark S. Zeiner It is certified that error appears in the above-indentified patent and that said Letters Patent is hereby corrected as shown below:

Column 1, line 12, "or" should be --of--;

Column 1, line 34, "staplers" should be --staples--;

Column 1, line 40, "Provide" should be --provide--;

Column 1, line 64, "other" should be --of the--;

Column 2, line 7, delete second instance of "of";

Column 2, lines 40-41, "aspects" should be --aspect--;

Column 4, line 18, "760" should be --70--;

Column 5, line 42, "removable" should be --removal--;

Column 8, line 6, "driers" should be --drivers--;

Column 9, line 12, "position" should be --direction--.

Signed and Sealed this

Eighth Day of August, 1995

*Attest:*

*Attesting Officer*

BRUCE LEHMAN

*Commissioner of Patents and Trademarks*